United States Patent
Shokri et al.

(10) Patent No.: US 10,167,342 B2
(45) Date of Patent: Jan. 1, 2019

(54) PRODUCTION OF HERSINTUZUMAB: A NEW HUMANIZED ANTIBODY AGAINST HER2 FOR CANCER TREATMENT

(71) Applicants: Fazel Shokri, Tehran (IR); Mahmood Jeddi-Tehrani, Tehran (IR); Mohammad Mehdi Amiri, Tehran (IR)

(72) Inventors: Fazel Shokri, Tehran (IR); Mahmood Jeddi-Tehrani, Tehran (IR); Mohammad Mehdi Amiri, Tehran (IR)

( * ) Notice: Subject to any disclaimer, the term of this patent is extended or adjusted under 35 U.S.C. 154(b) by 64 days.

(21) Appl. No.: 15/249,910

(22) Filed: Aug. 29, 2016

(65) Prior Publication Data

US 2017/0066829 A1    Mar. 9, 2017

(51) Int. Cl.
| | |
|---|---|
| A61K 39/00 | (2006.01) |
| A61K 39/395 | (2006.01) |
| C07K 16/28 | (2006.01) |
| C07K 16/32 | (2006.01) |
| C07K 16/30 | (2006.01) |
| A61K 47/48 | (2006.01) |

(52) U.S. Cl.
CPC ........ *C07K 16/32* (2013.01); *A61K 47/48569* (2013.01); *C07K 2317/24* (2013.01); *C07K 2317/33* (2013.01); *C07K 2317/73* (2013.01)

(58) Field of Classification Search
None
See application file for complete search history.

(56) References Cited

U.S. PATENT DOCUMENTS 9,327,035 B2    5/2016  Fuh et al.

FOREIGN PATENT DOCUMENTS

| | | |
|---|---|---|
| WO | 2001005425 A2 | 1/2001 |
| WO | 2009123894 A2 | 10/2009 |

*Primary Examiner* — Julie Wu
(74) *Attorney, Agent, or Firm* — NovoTechIP International PLLC (57) ABSTRACT

A monoclonal anti-HER2 antibody is mutated on complementarity determining regions (CDRs) and framework regions. The VH domain of the antibody includes a portion of the amino acid sequence as SEQ ID NO: 1. The VL domain of the antibody includes a portion of the amino acid sequence as SEQ ID NO: 5.

14 Claims, 4 Drawing Sheets

Specification includes a Sequence Listing.

SEQUENCE LISTING

<160> NUMBER OF SEQ ID NOS: 8

<210> SEQ ID NO 1
<211> LENGTH: 116
<212> TYPE: PRT
<213> ORGANISM: Artificial Sequence
<220> FEATURE:
<223> OTHER INFORMATION: Synthetic Hersintuzumab heavy chain variable
      domain

<400> SEQUENCE: 1

Glu Val Lys Leu Val Glu Ser Gly Gly Gly Leu Val Lys Pro Gly Gly
1               5                   10                  15

Ser Leu Arg Leu Ser Cys Ala Thr Ser Gly Phe Ser Phe Ser Ser Tyr
            20                  25                  30

Tyr Met Tyr Trp Val Arg Gln Ala Pro Gly Lys Arg Leu Glu Trp Val
        35                  40                  45

Ala Tyr Ile Ser Ser Gly Ser Glu Ile Tyr Tyr Ser Asp Ser Val Lys
    50                  55                  60

Gly Arg Phe Thr Ile Ser Arg Asp Ser Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Leu Gly Asp Asp Gly Met Asp Val Trp Gly Gln Gly Thr Thr Val
            100                 105                 110

Thr Val Ser Ser
        115

<210> SEQ ID NO 2
<211> LENGTH: 5
<212> TYPE: PRT
<213> ORGANISM: Artificial Sequence
<220> FEATURE:
<223> OTHER INFORMATION: Synthetic CDR-H1= residues 31-35

<400> SEQUENCE: 2

Ser Tyr Tyr Met Tyr
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic CDR-H2= residues 50-65

<400> SEQUENCE: 3

Tyr Ile Ser Ser Gly Ser Glu Ile Tyr Tyr Ser Asp Ser Val Lys Gly
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: Synthetic CDR-H3= residues 95-102

<400> SEQUENCE: 4

Leu Gly Asp Asp Gly Met Asp Val
1               5

<210> SEQ ID NO 5
<211> LENGTH: 107

```
<212> TYPE: PRT
<213> ORGANISM: Artificial Sequence
<220> FEATURE:
<223> OTHER INFORMATION: Synthetic Hersintuzumab light chain variable
      domain:

<400> SEQUENCE: 5

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Asn Val Arg Thr Ala
            20                  25                  30

Val Ala Trp Phe Gln Gln Lys Pro Gly Lys Ala Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Phe Cys Leu Gln His Asn Ser Tyr Pro Leu
                85                  90                  95

Thr Phe Gly Gly Gly Thr Lys Val Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: Synthetic CDR-L1= residues 24-34

<400> SEQUENCE: 6

Arg Ala Ser Gln Asn Val Arg Thr Ala Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic CDR-L2= residues 50-56

<400> SEQUENCE: 7

Leu Ala Ser Asn Arg His Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic CDR-L3= residues 89-97

<400> SEQUENCE: 8

Leu Gln His Asn Ser Tyr Pro Leu Thr
1               5
```

PRODUCTION OF HERSINTUZUMAB: A NEW HUMANIZED ANTIBODY AGAINST HER2 FOR CANCER TREATMENT

CROSS REFERENCE TO RELATED APPLICATION

This application claims the benefit of priority to an Iran patent application having serial number 139450140003006215 filed on Aug. 31, 2015, which is incorporated by reference herein in its entirety.

TECHNICAL FIELD

The present disclosure relates to the field of biotechnology. In particular, the present application relates to a humanized monoclonal anti-HER2 antibody, the preparation method and use thereof.

BACKGROUND

Breast cancer is one of the most common malignant tumors in women. More than one million new cases of breast cancer occur worldwide annually, and nearly 400 thousand people die from breast cancer every year. In recent years, the worldwide incidence of breast cancer showed a clear upward trend. Notwithstanding whether the incidence of breast cancer generally higher or lower than average in a particular region, the incidence of breast cancer is increasing at a rate of 5-20%. The growth trend of the incidence of breast cancer in Asian women has been significantly higher than that in the United States and Europe. In some cities in China, breast cancer has become the primary malignant tumor in women. Conventional treatments for breast cancer include surgery, chemotherapy and endocrine therapy and so on. Although these conventional treatments may prolong survival in patients to a large extent, their side effects are often serious. Also, the therapeutic effect of many may be hard to further improve. Targeted cancer therapy is a new treatment for cancer that has arisen in recent years. A representative of targeted cancer therapy is antitumor monoclonal antibody therapy.

HER2 (human epidermal growth factor receptor 2) is a transmembrane protein with tyrosine kinase activity, having a molecular weight of about 185 KD. Anti-HER2 humanized monoclonal antibody specifically bind to HER2, and may have antitumor mechanisms as follows: specifically binding to the extracellular domain of HER2 receptor to block the constitutive activation of HER2 homodimers and interfere the heterodimer formation of HER2 with other ErbB family members; mediating the endocytosis and the degradation in lysosomes of HER2 receptor; activating PTEN (phosphatase and tensin homology) and blocking PI3K (Phosphatidylinositol 3-kinase) signal channel; inhibiting tumor cell proliferation by regulation of cell cycle; promoting tumor cell apoptosis; inhibiting tumor angiogenesis; ADCC (antibody-dependent cell-mediated cytotoxicity) effect; inhibiting DNA repair; increasing the cytotoxicity of chemotherapeutic agents; reversing the resistance of tumor cells to the killing effects of host cell factors, and etc.

Trastuzumab (trade name: Herceptin) is a humanized anti-HER2 antibody that maintains the murine CDR regions and a small amount of murine FR residues, which has been used to treat patients with HER2 overexpressing metastatic breast cancer as single drug. This drug may be used in combination with paclitaxel or anthracyclines (doxorubicin or epirubicin) plus cyclophosphamide in clinic as first-line drugs to treat HER2 overexpressing metastatic breast cancer. Because of primary or acquired resistance to Trastuzumab, combination therapy of Trastuzumab and Pertuzumab use for treatment of breast cancer.

SUMMARY

Disclosed subject matter includes a humanized monoclonal anti-HER2 antibody that can be used for treating cancer. The antibody (Hersintuzumab) specifically binds the extracellular domain of HER2. Hersintuzumab binds to cell surface-associated HER2 with an affinity comparable to that of Trastuzumab (Herceptin®).

Methods for producing humanized antibodies, particularly humanized anti-HER2 antibodies are known. The disclosed antibody was derived from a murine monoclonal anti-HER2 antibody. The humanized antibody preferably has one or more amino acid residues introduced into it from a source that is non-human.

The antibody is mutated on complementarity determining regions (CDR) and framework regions to keep the affinity steady compared to murine antibody. By gene synthesis technique, the humanized anti-HER2 antibody, Hersintuzumab, is fabricated. The VH and VL sequences as well as the CDRs of the humanized anti-HER2 antibody are indicated below:

```
Hersintuzumab heavy chain variable domain of SEQ ID NO: 1:
        10          20          30          40          50          60
EVKLVESGGG LVKPGGSLRL SCATSGFSFS SYYMYWVRQA PGKRLEWVAY ISSGSEIYYS 70          80          90         100         110
DSVKGRFTIS RDSAKNTLYL QMNSLRAEDT AVYYCARLGD DGMDVWGQGT TVTVSS
SEQ ID NO: 2 = CDR-H1 = residues 31-35 of SEQ ID NO: 2 (SYYMY)
SEQ ID NO: 3 = CDR-H2 = residues 50-65 of SEQ ID NO: 3
(YISSGSEIYYSDSVKG)
SEQ ID NO: 4 = CDR-H3 = residues 98-105 of SEQ ID NO: 1 (LGDDGMDV)

Hersintuzumab light chain variable domain of SEQ ID NO: 5:
        10          20          30          40          50          60
DIVMTQSPSS LSASVGDRVT ITCRASQNVR TAVAWFQQKP GKAPKALIYL ASNRHTGVPD 70          80          90         100
RFTGSGSGTE FTLTISNLQP EDFATYFCLQ HNSYPLTFGG GTKVEIK
SEQ ID NO: 6 = CDR-L1 = residues 24-34 of SEQ ID NO: 5
(RASQNVRTAVA)
SEQ ID NO: 7 = CDR-L2 = residues 50-56 of SEQ ID NO: 5 (LASNRHT)
SEQ ID NO: 8 = CDR-L3 = residues 89-97 of SEQ ID NO: 5 (LQHNSYPLT)
```

Provided herein are isolated monoclonal antibodies that bind HER2, such as cell-surface or soluble HER2. In some instances, the VH domain of the antibody comprises at least a portion of the amino acid sequence set forth herein as SEQ ID NO: 1, such as one or more (such as all three) CDR sequences from SEQ ID NO: 1. In some instances the VL domain of the antibody comprises at least a portion of the amino acid sequence set forth herein as SEQ ID NO: 5, such as one or more (such as all three) CDR sequences from SEQ ID NO: 5.

Further provided herein are isolated conjugates comprising a HER2-specific monoclonal antibody and an effector molecule. In some instances, the effector molecule can be a drug, such as a small molecule drug. In other instances, the effector molecule can be a toxin, such as *Pseudomonas* exotoxin or a variant thereof. In yet other instances, the effector molecule can be a detectable label. In some examples, the detectable label can be a fluorescence, enzymatic, or radioactive label. Also provided by the present disclosure are compositions comprising a therapeutically effective amount of a disclosed HER2 antibody and a pharmaceutically acceptable carrier.

BRIEF DESCRIPTION OF THE DRAWINGS

Features of the subject technology are set forth in the appended claims. However, for purpose of explanation, several implementations of the subject technology are set forth in the following figures.

DETAILED DESCRIPTION

In the following detailed description, various examples are presented to provide a thorough understanding of inventive concepts, and various aspects thereof that are set forth by this disclosure. However, upon reading the present disclosure, it may become apparent to persons of skill that various inventive concepts and aspects thereof may be practiced without one or more details shown in the examples. In other instances, well known procedures, operations and materials have been described at a relatively high-level, without detail, to avoid unnecessarily obscuring description of inventive concepts and aspects thereof.

Unless otherwise noted, technical terms are used according to conventional usage.

In order to facilitate review of the various instants of the disclosure, the following explanations of specific terms are provided:

The term "antibody," as used herein, means a polypeptide ligand comprising at least a light chain or heavy chain immunoglobulin variable region which recognizes and binds (such as specifically recognizes and specifically binds) an epitope of an antigen, such as HER2, or a fragment thereof. Immunoglobulin molecules are composed of a heavy and a light chain, each of which has a variable region, termed the variable heavy (VH) region and the variable light (VL) region. Together, the VH region and the VL region are responsible for binding the antigen recognized by the antibody.

Antibodies include intact immunoglobulins and the variants and portions of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. It will be understood that the term "antibody," as used herein, also encompasses genetically engineered forms such as chimeric and humanized antibodies and hetero-conjugate antibodies (such as bi-specific antibodies and drug- or toxin-conjugated antibodies).

Typically, a naturally occurring immunoglobulin has heavy (H) chains and light (L) chains interconnected by disulfide bonds. There are two types of light chain, lambda (λ) and kappa (κ). There are five main heavy chain classes (or iso-types) that determine functional activity of an antibody molecule, the five being IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a framework region interrupted by three hypervariable regions, also called "complementarity-determining regions" or "CDRs." The extent of the framework region and CDRs has been defined according to Kabat et al. The Kabat database is maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or H-CDR3) is located in the variable domain of the heavy chain of the antibody in which it is found, whereas a $V_L$ CDR1 (or L-CDR1) is the CDR1 from the variable domain of the light chain of the antibody in which it is found. An antibody that binds HER2, for example, will have a specific $V_H$ region and the $V_L$ region sequence, and thus specific CDR sequences. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include mouse, chimeric and humanized monoclonal antibodies.

A human antibody is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a non-human antibody also called a "humanized" antibody. A "humanized" immunoglobulin is an immunoglobulin including a human framework region and one or more CDRs from a non-human (for example a mouse, rabbit, rat, or synthetic) immunoglobulin. The non-human immunoglobulin providing the CDRs is termed a "donor," and the human immunoglobulin providing the framework is termed an "acceptor." In one aspect, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. Antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. Chimeric antibodies of interest herein include primatized antibodies comprising variable domain antigen-binding sequences derived from a non-human primate (e.g. Old World Monkey, Ape etc.) and human constant region sequences.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

The term "chemotherapeutic agent" as used herein refers to a chemical compound useful in the treatment of cancer. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK7; razoxane; sizofiran; spirogermanium; tenuazonic acid; triaziquone; 2, 2',2'=-trichlorotriethylamine; urethan; vindesine; dacarbazine; mannomustine; mitobronitol; mitolactol; pipobroman; gacytosine; arabinoside; cyclophosphamide; thiotepa; taxanes, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO)); retinoic acid; esperamicins; capecitabine; and pharmaceutically acceptable salts, acids or derivatives of any of the above. Also included in this definition of "chemotherapeutic agent" are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, onapristone, and toremifene; and anti-androgens such as flutamide, nilutamide, bicalutamide, leuprolide, and goserelin; and pharmaceutically acceptable salts, acids or derivatives of any of the above.

A "liposome" is a small vesicle composed of various types of lipids, phospholipids and/or surfactants. The liposome is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes. A "small molecule" is defined herein to have a molecular weight below about 500 Daltons.

The term "antibody-drug conjugate" (also "ADC") as used herein means a molecule that includes an antibody (or antigen-binding fragment of an antibody) conjugated to a drug, such as a cytotoxic agent. ADCs can be used, for example, to specifically target a cytotoxic agent to cancer cells through specific binding of the antibody to a tumor antigen expressed on the cell surface. Exemplary drugs for use with ADCs include anti-microtubule agents (such as maytansinoids, auristatin E and auristatin F) and interstrand crosslinking agents (e.g., pyrrolobenzodiazepines; PDBs).

The term "binding affinity" as used herein means affinity of an antibody for an antigen. In one aspect, affinity can be calculated by a modification of the Scatchard method described by Frankel et al. In addition, binding affinity can be measured by an antigen/antibody dissociation rate. In another aspect, a high binding affinity can be measured by a competition radioimmunoassay. Also, binding affinity can be measured by ELISA.

The term "specifically binds," as used herein, in the context of an antibody that "specifically binds" an antigen (such as HER2), means an antibody that binds the antigen with high affinity and does not significantly bind other unrelated antigens.

The term "amino acid sequences" as used herein, means the unique sequence of amino acids that characterizes a given protein. The term "nucleic acid sequence," as used herein, means a succession of letters that indicate the order of nucleotides within a DNA (using GACT) or RNA (GACU) molecule.

Disclosed herein is a monoclonal antibody (Hersintuzumab) that specifically binds the extracellular domain of HER2. Hersintuzumab binds to cell surface-associated HER2 with an affinity comparable to that of Trastuzumab (Herceptin®), but binds to a different epitope.

Methods for producing humanized antibodies, particularly humanized anti-HER2 antibodies are known. The disclosed antibody can be derived from a murine monoclonal anti-HER2 antibody. The humanized antibody preferably has one or more amino acid residues introduced into it from a source which is non-human. The non-human amino acid residues are often referred to as "import" residues, and are typically taken from an "import" variable domain. Humanization was essentially performed by substituting hypervariable region sequences for corresponding sequences of a human antibody. According to the so-called "best-fit" method, the sequence of the variable domain of a rodent antibody was screened against the entire library of known human variable-domain sequences. The human sequence which is closest to that of the rodent was then accepted as the human framework region (FR) for the humanized antibody. It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected, without undue experimentation, and combined from the recipient and import sequences so that the desired antibody characteristic, such as increased affinity for the target antigen(s), can be achieved. In general, the hypervariable region residues are directly and most substantially involved in influencing antigen binding.

In an aspect, the antibody can then be mutated on complementarity determining regions (CDR) and framework regions to keep the affinity steady compared to murine antibody. By gene synthesis technique, the humanized anti-HER2 antibody, Hersintuzumab, can be fabricated. The CDRs of the humanized anti-HER2 antibody are indicated below:

```
Hersintuzumab heavy chain variable domain SEQ ID NO: 1:
         10         20         30         40         50         60
EVKLVESGGG LVKPGGSLRL SCATSGFSFS SYYMYWVRQA PGKRLEWVAY ISSGSEIYYS 70         80         90        100        110
DSVKGRFTIS RDSAKNTLYL QMNSLRAEDT AVYYCARLGD DGMDVWGQGT TVTVSS
SEQ ID NO: 2 = CDR-H1 = residues 31-35 of SEQ ID NO: 1 (SYYMY)
SEQ ID NO: 3 = CDR-H2 = residues 50-65 of SEQ ID NO: 1
(YISSGSEIYYSDSVKG)
SEQ ID NO: 4 = CDR-H3 = residues 98-105 of SEQ ID NO: 1 (LGDDGMDV)

Hersintuzumab light chain variable domain SEQ ID NO: 5:
         10         20         30         40         50         60
DIVMTQSPSS LSASVGDRVT ITCRASQNVR TAVAWFQQKP GKAPKALIYL ASNRHTGVPD
         70         80         90        100
RFTGSGSGTE FTLTISNLQP EDFATYFCLQ HNSYPLTFGG GTKVEIK
SEQ ID NO: 6 = CDR-L1 = residues 24-34 of SEQ ID NO: 5
(RASQNVRTAVA)
SEQ ID NO: 7 = CDR-L2 = residues 50-56 of SEQ ID NO: 5 (LASNRHT)
SEQ ID NO: 8 = CDR-L3 = residues 89-97 of SEQ ID NO: 5 (LQHNSYPLT)
```

Provided herein are isolated monoclonal antibodies that bind (for example, specifically bind) HER2, such as cell-surface or soluble HER2. In some instants, the VH domain of the antibody comprises at least a portion of the amino acid sequence set forth herein as SEQ ID NO: 1, such as one or more (such as all three) CDR sequences from SEQ ID NO: 1. In some instances the VL domain of the antibody comprises at least a portion of the amino acid sequence set forth herein as SEQ ID NO: 5, such as one or more (such as all three) CDR sequences from SEQ ID NO: 5.

In some examples, the VH domain of the antibody that binds HER2 comprises amino acid residues 31-35, 50-65 and 98-105 of SEQ ID NO: 1 and/or the VL domain of the antibody comprises amino acid residues 24-34, 50-56 and 89-97 of SEQ ID NO: 5. In some examples, the amino acid sequence of the VH domain is at least 90% identical to SEQ ID NO: 1; and/or the amino acid sequence of the VL domain is at least 90% identical to SEQ ID NO: 5. In particular examples, the VH domain of the antibody comprises SEQ ID NO: 1 and/or the VL domain of the antibody comprises SEQ ID NO: 5.

In some examples, the antibody is a Fab fragment, a Fab' fragment, a F(ab)'2 fragment, a single chain variable fragment (scFv), or a disulfide stabilized variable fragment (dsFv).

Further provided herein are isolated conjugates comprising a Her2-specific monoclonal antibody and an effector molecule. In some instants, the effector molecule can be a drug, such as a small molecule drug. In particular examples, the drug can be auristatin F. In other examples, the effector molecule can be a toxin, such as *Pseudomonas* exotoxin or a variant thereof. In yet other examples, the effector molecule can be a detectable label. In some examples, the detectable label can be a fluorescence, enzymatic, or radioactive label. Also provided by the present disclosure are compositions comprising a therapeutically effective amount of a disclosed HER2 antibody and a pharmaceutically acceptable carrier. Further provided are compositions comprising a therapeutically effective amount of a conjugate disclosed herein and a pharmaceutically acceptable carrier.

Figure 1:
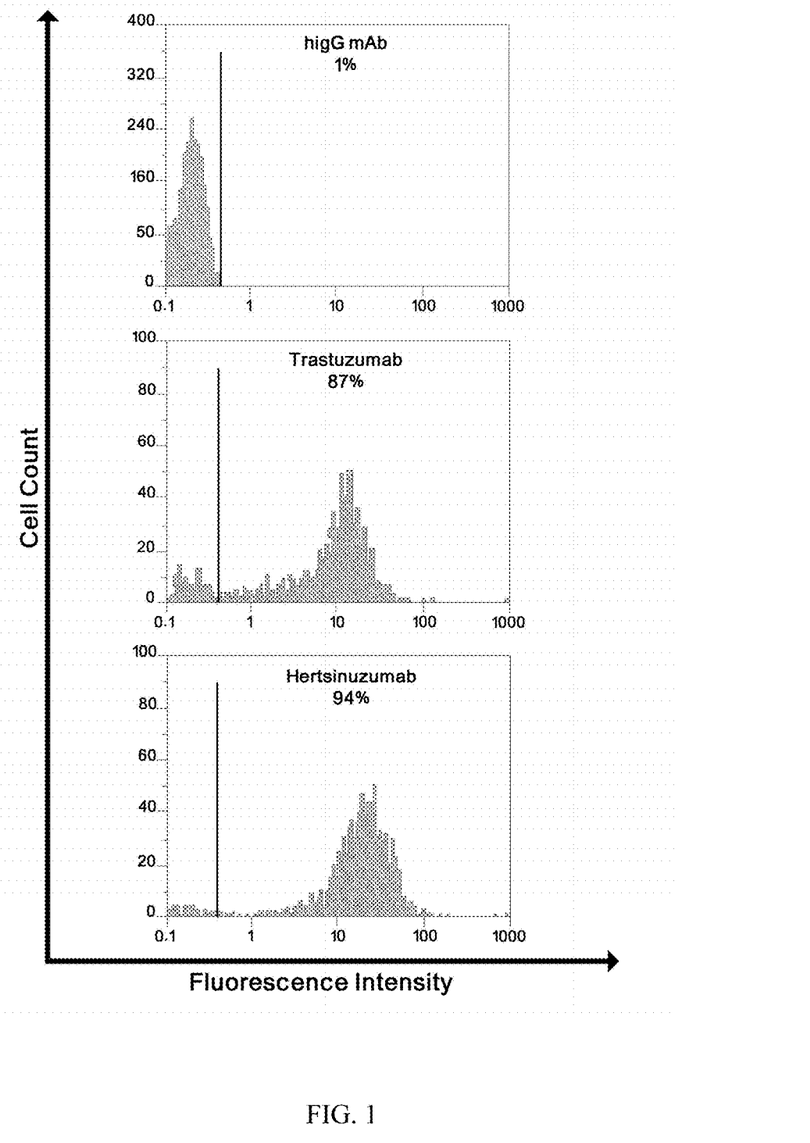
FIG. 1 illustrates the binding of humanized anti-HER2 antibody on HER2 positive cancer cells, according to a preferred implementation of the instant application.

Human breast cancer cells BT-474 were mixed with 10 micrograms per milliliter of the humanized Hersintuzumab, Trastuzumab and IgG as negative control. Following incubation for 1 hour and at 4° C., the cells were incubated with anti-immunoglobulin antibody and rinsed. As shown on FIG. 1, besides Trastuzumab, the Hersintuzumab is also capable of binding to human HER2 on BT-474 cancer cells.

Figure 2:
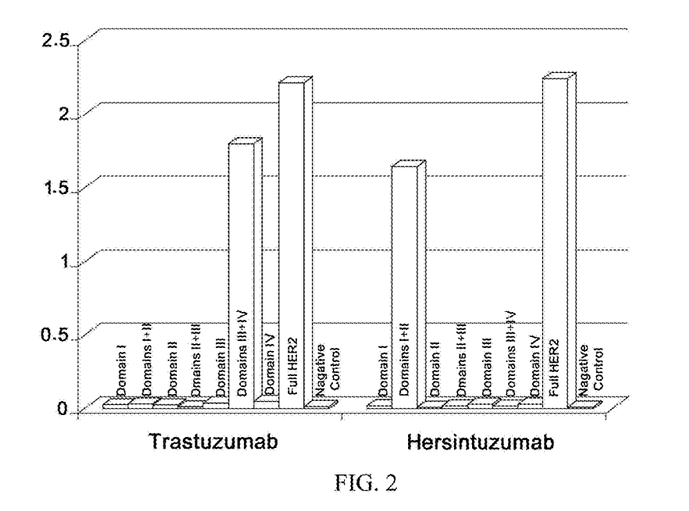
FIG. 2 illustrates the binding of the humanized anti-HER2 antibody to HER2 domains, according to an implementation.

FIG. 2 illustrates results of binding the Hersintuzumab to HER-2 and compares it with the effect of Trastuzumab on HER2. 7 Domains namely I, II, III, IV, I+II, II+III, and III+IV were inserted to pSecTag/Hygro vector and then transfected to CHO cells. Ten microgram of Hersintuzumab and Trastuzumab were coated in micotiter ELISA plate. Supernatant of transient transfection of each domain was added into coated wells. Wells were then incubated with HRP-conjugated anti-His-Tag antibody. After the final wash step, TMB substrate solution was added followed by stop solution. The OD values were measured at 450 nm. As shown on FIG. 2 Trastuzumab bound with the domain III+IV and Hersintuzumab with domains I+II which shows that the epitope of Hersintuzumab is located in domains I+II or between domains I and II.

Figure 3:
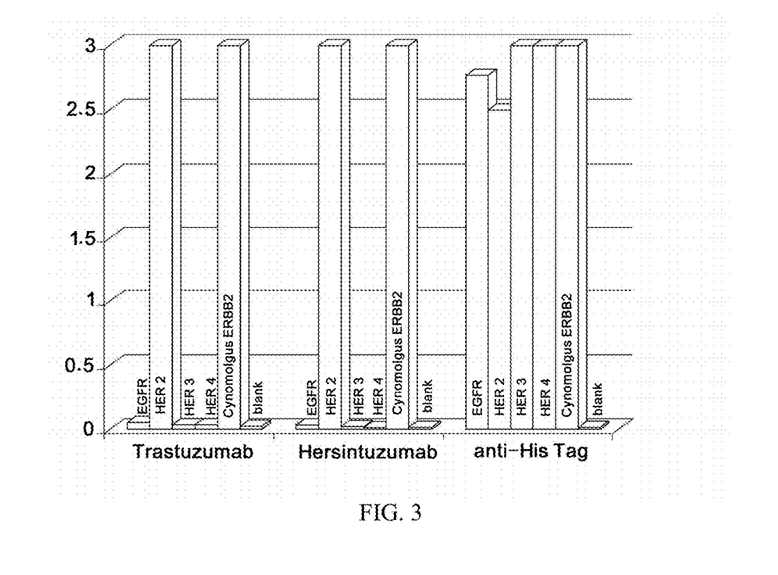
FIG. 3 illustrates the binding of the humanized anti-HER2 antibody to Ape's HER2 and other human EGFR family members, according to an implementation.

FIG. 3 illustrates results of binding the Hersintuzumab to other members of the EGFR family. Ape's ERBB2 and human's HER1, HER3 and HER4 were incubated on ELISA micro-plates for 1.5 hours and at 37° C. Further, HRP-conjugated monoclonal Trastuzumab and Hersintuzumab antibodies were added to them and the reaction was stopped. The color of the samples was read by an ELISA-reader at 450 nano-meter wavelength. As seen in FIG. 3 the monoclonal Hersintuzumab and Trastuzumab are only capable of binding to Ape and human ERBB2. It should be noted that all of the samples have poly-histidine at one end and react to monoclonal anti His-Tag antibody.

Figure 4:
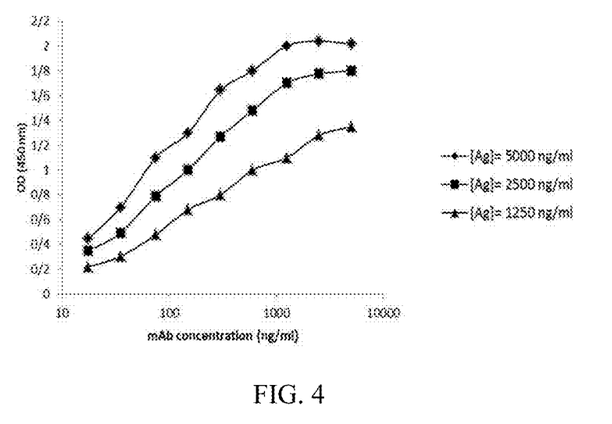
FIG. 4 shows the affinity of the humanized anti-HER2 antibody to HER2 molecule.

FIG. 4 illustrates results of the affinity of the antibody based on ELISA. Different solutions of HRP-conjugated Hersintuzumab antibody were studied by an ELISA-reader at 450 nano-meter wavelength and the correlated sigmoidal curves were drawn based on OD versus Hersintuzumab antibody logarithmic concentrations. The resulted affinity for this humanized anti-HER2 Hersintuzumab antibody is 0.6 $nM^{-1}$.

Figure 5:
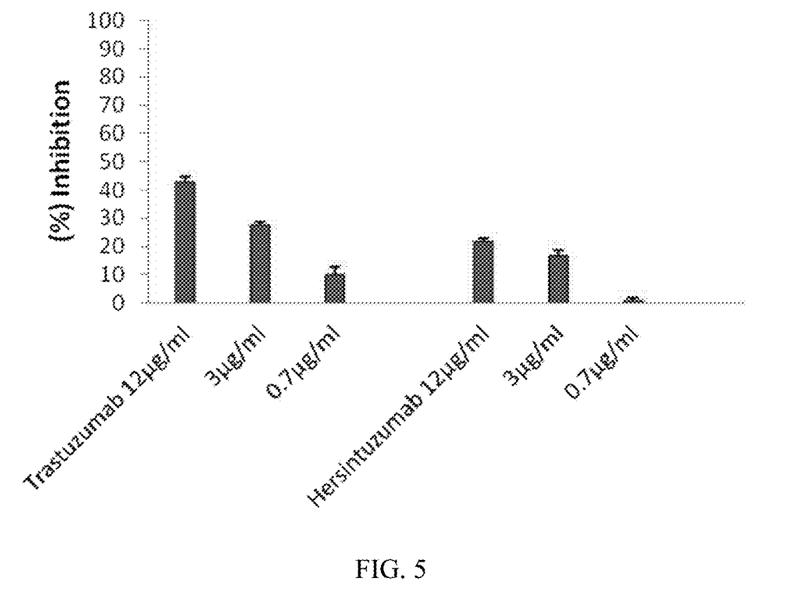
FIGS. 5 and 6 illustrate the effect of humanized anti-HER2 antibody on cellular proliferation as compared to the commercial anti-HER2 antibodies: Trastuzumab and Pertuzumab.
Figure 6:
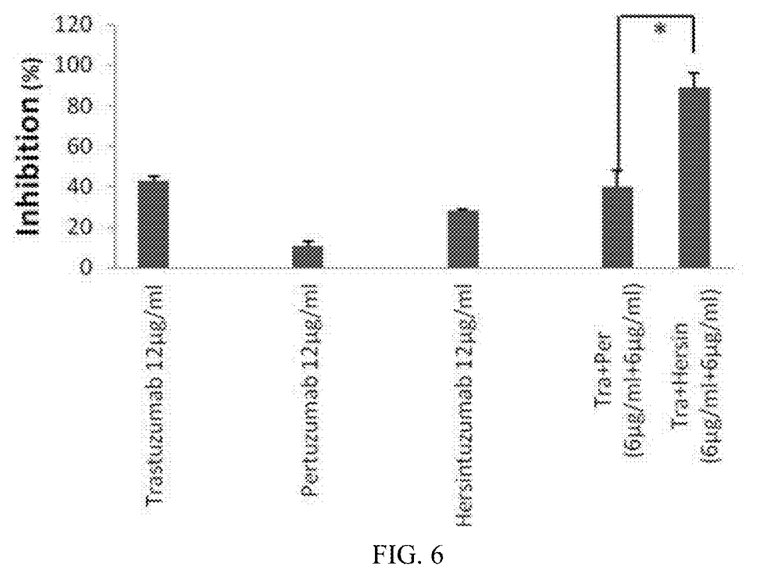

FIGS. 5 and 6 Inhibition of cellular proliferation of cancer cells was studied. 50,000 cancer cells (BT-474) were grown on 96 plates. After adding different concentrations of antibodies (Hersintuzumab, Trastuzumab, Pertuzumab and combinations thereof), the mixtures were incubated for 72 hours and were placed within radioactive Thymidine for 8 hours. The samples were measured by a beta-counter and the results are illustrated in FIGS. 5 and 6. As shown in FIGS. 5 and 6, Hersintuzumab as well as Trastuzumab can effectively induce a dose-dependent inhibition of cell proliferation on BT-474 cells.

In an aspect, combination of Trastuzumab and Hersintuzumab may be more effective in inhibition of cellular proliferation compared to combination of Pertuzumab and Trastuzumab.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

What is claimed is:

1. A humanized monoclonal anti-HER2 antibody for treating cancer, comprising:
   CDR-H1 comprising amino acid residues of 31-35 of SEQ ID NO: 1;
   CDR-H2 comprising amino acid residues of 50-65 of SEQ ID NO: 1;
   CDR-H3 comprising amino acid residues of 98-105 of SEQ ID NO: 1;
   CDR-L1 comprising amino acid residues of 24-34 of SEQ ID NO: 5;
   CDR-L2 comprising amino acid residues of 50-56 of SEQ ID NO: 5; and
   CDR-L3 comprising amino acid residues of 89-97 of SEQ ID NO: 5.

2. The humanized monoclonal anti-HER2 antibody of claim 1, further comprising:

(a) a heavy chain variable domain having at least 90% identity to the amino acid sequence of SEQ ID NO: 1;
(b) a light chain variable domain having at least 90% identity to the amino acid sequence of SEQ ID NO: 5; or
(c) a heavy chain variable domain according to (a) and a light chain variable domain according to (b).

3. The humanized monoclonal anti-HER2 antibody of claim 1, wherein the heavy chain variable domain is identical to SEQ ID NO: 1.

4. The humanized monoclonal anti-HER2 antibody of claim 1, wherein the light chain variable domain is identical to SEQ ID NO: 5.

5. The humanized monoclonal anti-HER2 antibody of claim 1, wherein the humanized monoclonal anti-HER2 antibody is a Fab fragment, a F(ab)'2 fragment, or a single chain variable fragment (scFv).

6. The humanized monoclonal anti-HER2 antibody of claim 1, wherein the humanized monoclonal anti-HER2 antibody is to treat breast cancer.

7. An antibody-drug conjugate for treating cancer comprising:
a humanized monoclonal anti-HER2 antibody conjugated to a drug, wherein the humanized monoclonal anti-HER2 antibody comprises:
CDR-H1 comprising amino acid residues of 31-35 of SEQ ID No: 1;
CDR-H2 comprising amino acid residues of 50-65 of SEQ ID No: 1;
CDR-H3 comprising amino acid residues of 98-105 of SEQ ID No: 1;
CDR-L1 comprising amino acid residues of 24-34 of SEQ ID No: 5;
CDR-L2 comprising amino acid residues of 50-56 of SEQ ID No: 5; and
CDR-L3 comprising amino acid residues of 89-97 of SEQ ID No: 5.

8. The antibody-drug conjugate of claim 7, wherein the drug includes a cytotoxic agent.

9. The antibody-drug conjugate of claim 8, wherein the humanized monoclonal anti-HER2 antibody specifically delivers the cytotoxic agent to cancer cells.

10. The antibody-drug conjugate of claim 8, wherein the humanized monoclonal anti-HER2 antibody is configured to specifically bind to a tumor antigen expressed on a cancer cell surface.

11. The antibody-drug conjugate of claim 7, wherein the drug includes an anti-microtubule agent.

12. The antibody-drug conjugate of claim 7, wherein the drug includes an interstrand cross-linking agent.

13. The antibody-drug conjugate of claim 7, wherein the antibody-drug conjugate is to treat breast cancer.

14. The humanized monoclonal anti-HER2 antibody of claim 1, wherein the humanized monoclonal anti-HER2 antibody in hetero-conjugation with trastuzumab is to treat breast cancer.

* * * * *